(12) United States Patent
Carletti et al.

(10) Patent No.: US 8,569,362 B2
(45) Date of Patent: Oct. 29, 2013

(54) POLYKETIDE MOLECULES AS ANTICANCER AGENTS

(75) Inventors: Isabelle Carletti, Toulouse (FR); Georges Massiot, Reims (FR); Cécile Debitus, Tahiti (PF)

(73) Assignees: Pierre Fabre Medicament, Boulogne-Billancourt (FR); Centre National de la Recherche Scientifique (CNRS), Paris (FR); Institut de Recherche pour le Development (IRD), Marseilles (FR)

( * ) Notice: Subject to any disclaimer, the term of this patent is extended or adjusted under 35 U.S.C. 154(b) by 0 days.

(21) Appl. No.: 13/504,797

(22) PCT Filed: Oct. 28, 2010

(86) PCT No.: PCT/EP2010/066334
§ 371 (c)(1),
(2), (4) Date: May 30, 2012

(87) PCT Pub. No.: WO2011/051380
PCT Pub. Date: May 5, 2011

(65) Prior Publication Data
US 2012/0252889 A1     Oct. 4, 2012

(30) Foreign Application Priority Data

Oct. 28, 2009  (FR) ...................................... 09 57594

(51) Int. Cl.
*A61K 31/351* (2006.01)
*C07D 309/02* (2006.01)

(52) U.S. Cl.
USPC ........... 514/460; 549/263; 549/273; 549/292; 514/449; 514/451

(58) Field of Classification Search
USPC ........... 549/263, 273, 292; 514/449, 451, 460
See application file for complete search history.

(56) References Cited

U.S. PATENT DOCUMENTS

| | | | |
|---|---|---|---|
| 6,833,367 B2 * | 12/2004 | Kinder et al. ............... | 514/231.5 |
| 7,214,708 B2 * | 5/2007 | Sundermann et al. ........ | 514/459 |
| 2003/0018013 A1 | 1/2003 | Dasseux et al. | |
| 2005/0004185 A1 | 1/2005 | Bachmann et al. | |

OTHER PUBLICATIONS

Kashman et al., "Ptilomycalin A: A Novel Polycyclic Guanidine Alkaloid of Marine Orgin", J. Am. Chem. Soc. 1989, 111, pp. 8925-8926.
Lajoie-Mazenc et al., "Recruitment of antigenic gamma-tubulin during mitosis in animal cells: presence of gamma-tubulin in the mitotic spindle", Journal of Cell Science 107, 1994, pp. 2825-2837.
Mudit et al., "Discovery, design, and synthesis of anti-metastatic lead phenylmethylene hydantoins inspired by marine natural products", Bioorganic & Medicinal Chemistry 17, 2009, pp. 1731-1738.

* cited by examiner

*Primary Examiner* — Golam M M Shameem
(74) *Attorney, Agent, or Firm* — Birch, Stewart, Kolasch & Birch, LLP

(57) ABSTRACT

The present invention relates to a polyketide molecule of the following formula (I):

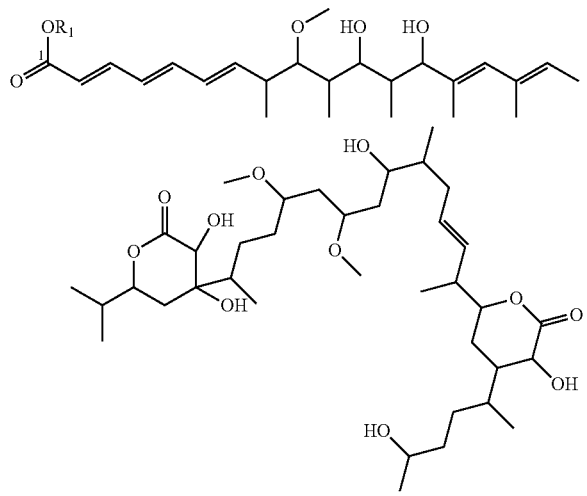

or a pharmaceutically acceptable salt thereof, where $R_1$ is a hydrogen atom or a ($C_1$-$C_7$) alkyl group, as well as the method of preparation and use thereof, in particular as an anticancer agent.

6 Claims, No Drawings

POLYKETIDE MOLECULES AS ANTICANCER AGENTS

The present invention relates to a molecule of polyketide type extracted from a sponge and analogues thereof, a method of extraction and hemi-synthesis and the use of said compounds as medicine, in particular for the treatment of cancer.

Since several decades, marine sponges have become the centre of numerous studies since the demonstration of their production of bioactive secondary metabolites, in particular alkaloids.

The inventors have thus been able to isolate a new molecule of polyketide type from the sponge *Hemimycale* sp. which has an anticancer activity.

The subject matter of the present invention is thus a compound of following formula (I):

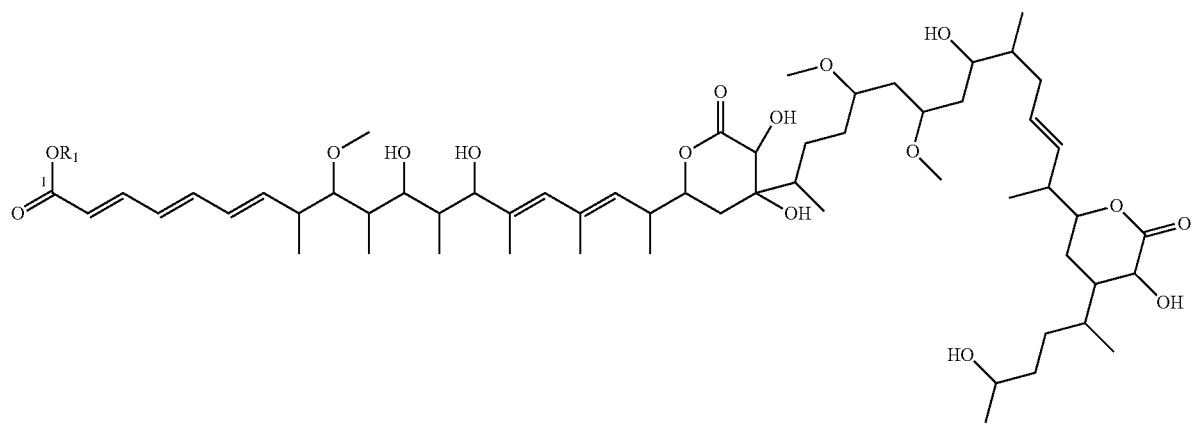

or a pharmaceutically acceptable salt thereof
where $R_1$ is a hydrogen atom or a ($C_1$-$C_7$) alkyl group, for example a ($C_1$-$C_4$) alkyl group, for example a methyl.

"($C_1$-$C_7$) alkyl" group is taken to mean, according to the present invention, a saturated linear or branched hydrocarbon chain comprising from 1 to 7, for example from 1 to 4, and in particular 1, carbon atoms. By way of example may be cited the groups methyl, ethyl, propyl, isopropyl, butyl, sec-butyl, tert-butyl, pentyl or hexyl. It could be in particular a methyl group.

In the present invention, "pharmaceutically acceptable" is taken to designate that which is useful in the preparation of a pharmaceutical composition that is generally safe, non toxic and neither biologically nor otherwise undesirable and which is acceptable for veterinary use just as for human pharmaceutical use.

"Pharmaceutically acceptable salts" of a compound is taken to designate salts that are pharmaceutically acceptable, as defined herein, and which have the desired pharmacological activity of the parent compound. It could more particularly be a base addition salt. Such salts are formed when an acid proton present in the parent compound is either replaced by a metal ion, for example an alkali metal ion, an alkaline earth metal ion or an aluminium ion, or coordinated with an organic or inorganic base. Acceptable organic bases include diethanolamine, ethanolamine, N-methylglucamine, triethanolamine, tromethamine and similar. Acceptable inorganic bases include aluminium hydroxide, calcium hydroxide, potassium hydroxide, sodium carbonate and sodium hydroxide.

Given the number of asymmetric atoms present in said molecule of formula (I), the latter may take different configurations. A compound according to the invention could be in particular a compound of structure defined by its mode of extraction, in particular obtainable by a method comprising the following successive steps:

(i) maceration of a lyophilisate of *Hemimycale* sp. sponge with chloroform then with a hydro-ethanolic solution (in particular 10/90 water/ethanol), followed by filtration to give a filtrate, then concentration of said filtrate to give an extract, (ii) partition of the extract obtained at the preceding step (i) between water and dichloromethane and separation of the resulting aqueous and organic phases, extraction of the aqueous phase with ethyl acetate and separation of the new resulting aqueous and organic phases, combining the two organic phases thereby obtained and concentration to give a desalinated extract (the inorganic salts having been eliminated in the aqueous phase), (iii) taking up the desalinated extract obtained at the preceding step (ii) with a hydro-methanolic solution (in particular 10/90 water/methanol) and hexane, recovery and concentration of the methanolic phase to give a methanolic extract, (iv) isolation of the compound of formula (I) with $R_1$=H from the methanolic extract obtained at the preceding step (iii), and (v) optionally esterification of the carboxylic acid at C-(1) to give a compound of formula (I) with $R_1$=($C_1$-$C_7$) alkyl and/or salification of the compound obtained at the preceding step (iv), and isolation of the compound thereby obtained from the reaction mixture.

Within the scope of this method, the sponge *Hemimycale* sp. used could more particularly originate from the Torres archipelago, Vanuatu.

The compound of formula (I) could more particularly be selected from:

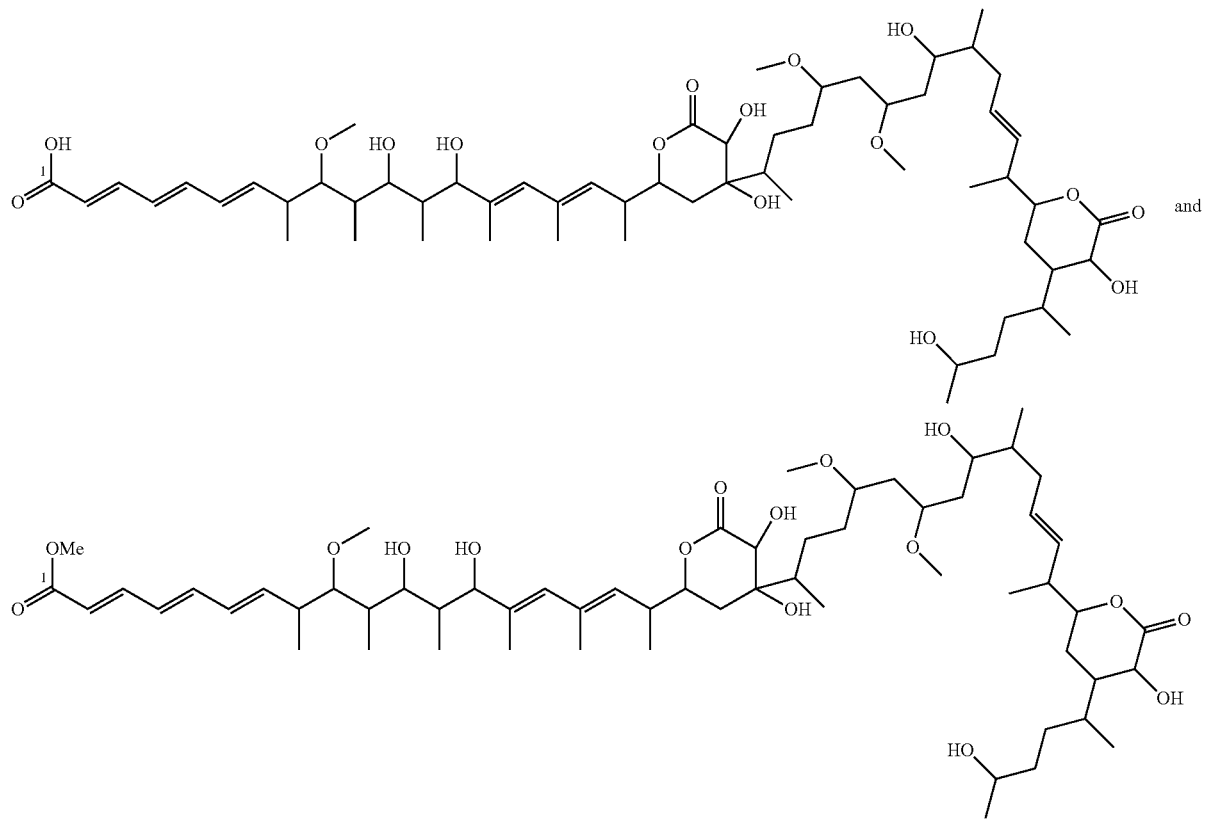

Another subject matter of the present invention is a compound of formula (I) as defined above for its use as medicine, in particular intended for the treatment of cancer.

The present invention also relates to the use of a compound of formula (I) as described previously for the preparation of a medicine, intended in particular for the treatment of cancer.

The invention also relates to a method of treating a proliferative disease, for example cancer, comprising the administration to a person in need thereof of an effective dose of a compound of formula (I) as defined above.

Another subject matter of the present invention is a pharmaceutical composition comprising at least one compound of formula (I) as defined above and a pharmaceutically acceptable excipient.

The pharmaceutical compositions of the invention could be formulated for example for administration by intravenous or oral route.

The compounds of the invention as active ingredients may be used at doses comprised between 0.01 mg and 1000 mg a day, for example in a single dose.

In a particular embodiment of the invention, the pharmaceutical composition is used as medicine, for example for the treatment of cancer.

Another subject matter of the present invention is a method of synthesizing a compound as defined previously, comprising the following successive steps:

(i) maceration of a lyophilisate of *Hemimycale* sp. sponge with chloroform then with a hydro-ethanolic solution (in particular 10/90 water/ethanol), followed by filtration to give a filtrate, then concentration of said filtrate to give an extract, (ii) partition of the extract obtained at the preceding step (i) between water and dichloromethane and separation of the resulting aqueous and organic phases, extraction of the aqueous phase with ethyl acetate and separation of the new resulting aqueous and organic phases, combining the two organic phases thereby obtained and concentration to give a desalinated extract, (iii) taking up the desalinated extract obtained at the preceding step (ii) with a hydro-methanolic solution (in particular 10/90 water/methanol) and hexane, recovery and concentration of the methanolic phase to give a methanolic extract, (iv) isolation of the compound of formula (I) with $R_1$=H from the methanolic extract obtained at the preceding step (iii), and (v) optionally esterification of the carboxylic acid at C-(1) to give a compound of formula (I) with $R_1$=($C_1$-$C_7$) alkyl and/or salification of the compound obtained at the preceding step (iv), and isolation of the compound thereby obtained from the reaction mixture.

The sponge used in this method could more particularly originate from the Torres archipelago, Vanuatu.

The isolation of the compound according to the invention with $R_1$=H (step iv) could be carried out in particular by silica gel chromatography. The product obtained could then be purified by techniques well known to those skilled in the art, and in particular by high performance liquid chromatography (HPLC).

The esterification of the carboxylic acid at step (v) could be carried out by protocols well known to those skilled in the art. In the case where it is wished to obtain a methyl ester, the reaction could be carried out in the presence of trimethylsilyldiazomethane ($TMSCHN_2$).

The step of salification of step (v) could be carried out by simple mixing of the compound with a pharmaceutically acceptable base, such as for example sodium or potassium hydroxide.

The compound thereby obtained could be separated from the reaction mixture by methods well known to those skilled in the art, such as for example by extraction, evaporation of the solvent or instead by precipitation and filtration.

The compound could moreover be purified if necessary by techniques well known to those skilled in the art, such as by recrystallisation if the compound is crystalline, by distillation, by silica gel chromatography or instead by high performance liquid chromatography (HPLC).

The subject matter of the present invention also relates to a method of synthesizing a compound as defined previously with $R_1$ representing a ($C_1$-$C_7$) alkyl group from a compound of formula (I) as defined previously with $R_1$=H, comprising the following successive steps:

(a) esterification of the carboxylic acid at C-(1) to give a compound of formula (I) with $R_1$=($C_1$-$C_7$) alkyl, (b) optionally salification of the compound obtained at the preceding step (a), and (c) isolation of the compound obtained at the preceding step (a) or (b) from the reaction mixture.

Step (a):

The esterification of the carboxylic acid could be carried out by protocols well known to those skilled in the art. In the case where it is wished to obtain a methyl ester, the reaction could be carried out in the presence of trimethylsilyldiazomethane (TMSCHN$_2$).

Step (b):

The step of salification could be carried out by simple mixing of the compound with a pharmaceutically acceptable base, such as for example sodium or potassium hydroxide.

Step (c):

The compound thereby obtained could be separated from the reaction mixture by methods well known to those skilled in the art, such as for example by extraction, evaporation of the solvent or instead by precipitation and filtration.

The compound could moreover be purified if necessary by techniques well known to those skilled in the art, such as by recrystallisation if the compound is crystalline, by distillation, by silica gel column chromatography or instead by high performance liquid chromatography (HPLC).

The invention is more particularly described in a non limiting manner in the examples that follow.

EXAMPLES

Example 1

Extraction of the Compound I-1 (Compound of Formula (I) with $R_1$=H)

5 kg of fresh *Hemimycale* sp. sponge were collected in the Torres archipelago in Vanuatu then lyophilised to give a lyophilisate of 650 g. The lyophilisate was successively macerated for 6 hours with chloroform then with a hydro-alcoholic solution (10:90 signifying 10% of water and 90% of ethanol). This second step was repeated twice. The filtrates obtained were combined together, filtered and concentrated using a rotary evaporator until an aqueous syrup was obtained. The latter was successively partitioned with dichloromethane and ethyl acetate in order to eliminate (in the aqueous phase) the inorganic salts from the extract. The desalinated extract (42 g) was taken up with a hydro-methanolic solution (10:90) and was then partitioned with hexane to eliminate the most apolar molecules. Two extracts, hexanic (24 g) and methanolic (18 g) were thereby obtained. Only the methanolic extract showed the pharmacological activity.

A monitoring method combining both pharmacological activity test and analysis and purification using liquid chromatography coupled to mass spectrometry (LC/MS) in negative electrospray ionisation mode (ESI–) equipped with a preparative split made it possible to highlight a family of molecules with m/z 1061.8; 1059.4; 1077.7; 1093.3 (+/–0.4 in ESI–) the most significant ion of which is m/z 1061.8.

A "flash" (or "stepwise") type chromatography on normal silica column was carried out on the methanolic extract with an increasing polarity elution of ethyl acetate and methanol in order to obtain 7 fractions. The fractions N° 4-7 that showed the pharmacological activity were then chromatographed on LH20 column with an elution of methanol. The final purifications were carried out by high performance liquid chromatography (HPLC) (RP C18) using a gradient of water and acetonitrile to obtain the active molecule of molecular weight 1062 (quantity 0.5 mg, yield 0.000077% with respect to the lyophilisate of the sponge); HRESITOFMS m/z 1061,6780 (M–H)$^-$, calculated for $C_{59}H_{97}O_{16}$ m/z 1061.6782.

(HRESITOFMS=high resolution electrospray ionization time of flight mass spectroscopy)

The molecule I-1 was thus obtained:

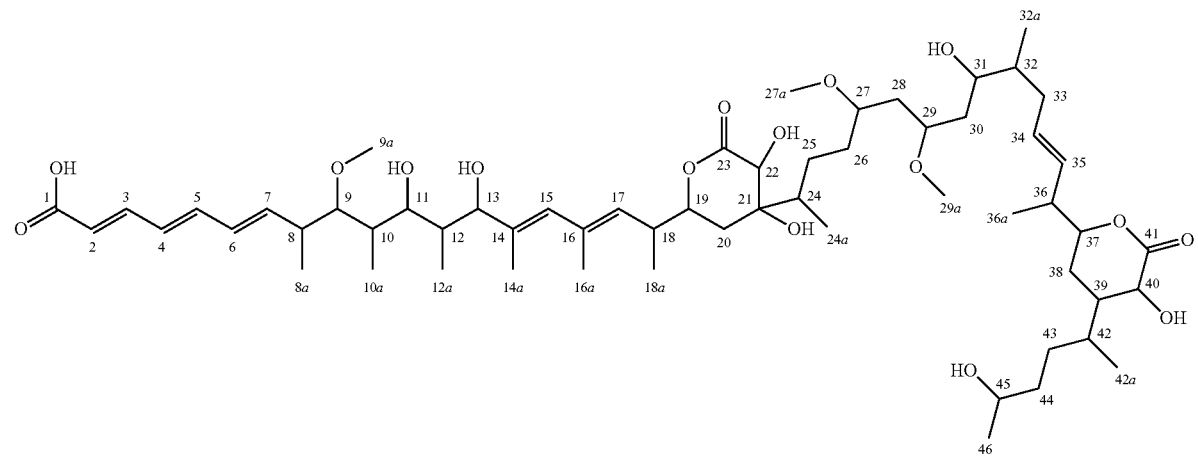 [SMILES: COC(CCC(C)C1(O)CC(C(C)/C=C(C)/C=C(\C)C(O)C(C)C(O)C(C)C(OC)C(C)/C=C/C=C/C=C/C(=O)O)OC(=O)C1O)CC(CC(O)C(C)C/C=C/C(C)C1CC(C(C)CCC(C)O)C(O)C(=O)O1)OC]

$^1$H NMR (500 MHz, METHANOL-$d_4$) δ=7.10 (1H, dd, J=15.1 Hz, J=11.1 Hz, H-3), 6.45 (1H, dd, J=15.0 Hz, J=10.7 Hz, H-5), 6.27 (1H, dd, J=15.0 Hz, J=11.0 Hz, H-4), 6.17 (1H, dd, J=15.3 Hz, J=10.7 Hz, H-6), 5.95 (1H, br. s., H-15), 5.90 (1H, d, J=15.3 Hz, H-2), 5.87 (1H, dd, J=15.1 Hz, J=8.7 Hz, H-7), 5.55 (1H, dt, J=14.8 Hz, J=7.3 Hz, H-34), 5.34 (1H, dd, J=15.3 Hz, J=8.5 Hz, H-35), 5.16 (1H, d, J=9.8 Hz, H-17), 4.42 (1H, ddd, J=11.3 Hz, J=7.5 Hz, J=3.5 Hz, H-19), 4.32 (1H, d, J=11.3 Hz, H-40), 4.27 (1H, s, H-22), 4.11 (1H, ddd, J=11.1 Hz, J=7.7 Hz, J=3.5 Hz, H-37), 3.99 (1H, d, J=7.3 Hz, H-13), 3.66-3.74 (2H, m, H-31, 45), 3.59-3.66 (1H, m, H-29), 3.57 (1H, dd, J=9.6 Hz, J=2.0 Hz, H-11), 3.40 (3H, s, H-29a), 3.39 (3H, s, H-9a), 3.33 (3H, s, H-27a), 3.32-3.34 (1H, m, H-27), 3.27 (1H, dd, J=6.7 Hz, J=4.6 Hz, H-9), 2.74-2.87 (1H, m, H-18), 2.48-2.61 (1H, m, H-8), 2.29-2.39 (1H, m, H-36), 2.20-2.27 (1H, m, H-33), 2.02-1.22 (22H, m, H-10, 12, 20, 24, 25, 26, 28, 30, 32, 33, 38, 39, 42, 43, 44), 1.82 (3H, s, H-16a), 1.69 (3H, s, H-14a), 1.15 (3H, d, J=6.4 Hz, H-46), 1.10 (3H, d, J=6.7 Hz, H-18a), 1.11 (3H, d, J=6.7 Hz, H-36a), 1.07 (3H, d, J=6.7 Hz, H-8a), 0.98-1.02 (1H, m, H-25), 0.96 (3H, d, J=6.7 Hz, H-24a), 0.93 (3H, d, H-12a), 0.91 (3H, d, J=7.0 Hz, H-42a), 0.89 (3H, d, J=6.7 Hz, H-32a), 0.85 (3H, d, J=7.0 Hz, H-10a)

$^{13}$C NMR (126 MHz, METHANOL-$d_4$) δ=178.4 (C-41), 177.0 (C-23), 174.1 (C-1), 142.8 (C-7), 142.7 (C-3), 139.8 (C-5), 137.4 (C-14), 135.4 (C-16), 133.2 (C-34), 132.5 (C-35), 131.7 (C-15), 131.6 (C-17), 130.9 (C-6), 130.7 (C-4), 127.6 (C-2), 88.3 (C-9), 82.8 (C-19), 82.1 (C-13), 80.9 (C-37), 79.1 (C-27), 77.0 (C-29), 76.4 (C-21), 75.5 (C-11), 72.5 (C-22), 72.0 (C-31), 68.7 (C-45), 68.2 (C-40), 59.6 (C-9a), 57.9 (C-29a), 56.5 (C-27a), 43.6 (C-36), 41.5 (C-8), 41.4 (C-39), 40.8 (C-26), 40.8 (C-28), 40.6 (C-32), 40.1 (C-10), 39.3 (C-18), 39.3 (C-24), 38.5 (C-12), 38.0 (C-44), 37.7 (C-33), 33.7 (C-42), 33.0 (C-30), 32.2 (C-20), 32.1 (C-43), 28.0 (C-25), 26.7 (C-38), 23.6 (C-46), 17.9 (C-16a), 17.2 (C-36a), 17.2 (C-18a, 8a), 14.4 (C-32a), 14.0 (C-14a), 13.4 (C-42a), 13.1 (C-24a), 13.0 (C-10a), 7.6 (C-12a)

Example 2

Preparation of the Methyl Ester I-2 from the Molecule I-1

To a 50 µg solution of the molecule I-1 solubilised in 50 µl of methanol was added a drop of trimethylsilyldiazomethane (TMSCHN$_2$). The reaction was left to stir for 10 minutes at ambient temperature to be finally dried with a light jet of nitrogen and analysed by LC/MS in ESI– mode. The reaction was total with the formation of the methyl ester, less polar, of m/z 1075.4 (M−H)$^-$.

Example 3

Growth Inhibition of a Panel of Human Cancer Cell Lines

The cancerous cells [lines A549 (non small cell lung cancer), BxPC3 (cancer of the pancreas), LoVo (colon cancer), MCF7 (breast cancer), Namalwa (Burkitt's lymphoma) and SK-OV-3 (ovarian cancer)] were cultured in a 96-well plate in RPMI 1640 medium without phenol red (Seromed) to which was added 10% of foetal veal serum (100 µl/well, 1 to 3.10$^4$ cells/ml depending on the considered line). After an incubation of 24 h at 37° C. in an incubator with 5% CO$_2$, the medium was replaced by that containing the compound to be tested (molecule I-1), after which the plates were incubated for an additional 48 h. Cell survival was evaluated by measurement of the luminescence after release of ATP in the medium using the cell lysis solutions, luciferase and luciferine contained in the ATP-lite-MTM kit, as recommended by the manufacturer (Packard, Rungis, France). Each experimental condition was tested at least three times in sextuplets. The table below presents the IC50 data (expressed in M) of the molecule I-1, as a function of the different cell lines tested.

| Cancer lines | A549 | BxPC3 | LoVo | MCF7 | Namalwa | SK-OV-3 |
|---|---|---|---|---|---|---|
| IC50 (M) | 8.2 · 10$^{-10}$ | 4.7 · 10$^{-10}$ | 8.1 · 10$^{-11}$ | 1.1 · 10$^{-11}$ | 1.1 · 10$^{-9}$ | 3.3 · 10$^{-10}$ |

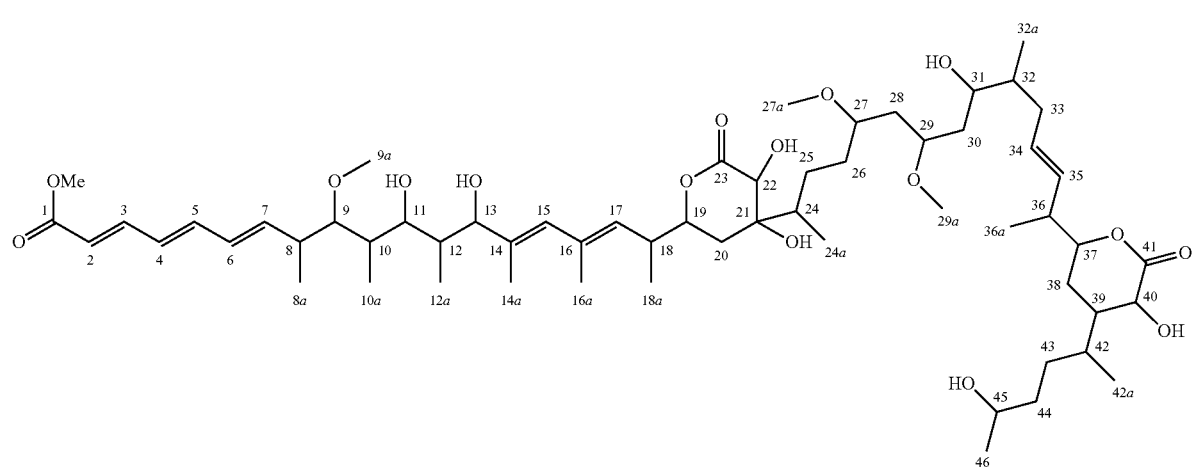 [SMILES: COC(=O)/C=C/C=C/C=C/C(C)C(OC)C(C)C(O)C(C)C(O)/C(C)=C/C(C)=C/C(C)C1CC(O)(C(C)CCC(CC(CC(O)C(C)C/C=C/C(C)C2CC(C(C)CCC(C)O)C(O)C(=O)O2)OC)OC)C(O)C(=O)O1]

Example 4

Description of Cellular Phenotype (Immunofluorescence and Microscopy)

The HeLa tumoral cells (human carcinoma) were cultured for 24 h on 12 mm diameter glass slides, placed in 24-well culture plates ($7.10^3$ cells per well).

The cells were then treated for a new period of 24 h by the molecule I-1 at the tested concentrations. At the end of the treatment, the slides were recovered and the cells were fixed and permeabilised as described previously (Lajoie-Mazenc I. et al., Journal of Cell Science 107, 2825-2837 (1994)). γ-tubulin and α-tubulin were then labelled (2 hours—37° C.) by specific primary antibodies diluted to 1/1000 (respectively: R75 rabbit polyclonal antibody (Lajoie-Mazenc I. et al.); clone B-5-1-2 monoclonal antibody, Sigma-Aldrich, France) then revealed by the corresponding fluorescent secondary antibodies (Alexa-568 anti-mouse and Alexa-488 anti-rabbit diluted to 1/1000; 45 min—37° C.). The DNA was labelled with DAPI (0.2 µg/ml—15 minutes—37° C.). After the different labellings, the slides were dried and mounted in a Vectashield mounting liquid (AbCys, France), before being observed through an epi-fluorescence microscope (Axiovert 200M; objective×63 Plan Apochromat NA, 1.4; ZEISS, France).

Between $5.10^{-9}$M and $5.10^{-8}$M, the interphasic cells were devoid of microtubular cytoskeleton (labelling by α-tubulin). The centrosomes were often separated and normally labelled by γ-tubulin.

With a dose effect between $10^{-9}$M and $5.10^{-8}$M, the mitotic cells were blocked in prometaphase without microtubules (α-tubulin labelling). The two centrosomes separated were normally present and labelled by γ-tubulin.

The invention claimed is:

1. A compound of following formula (I):

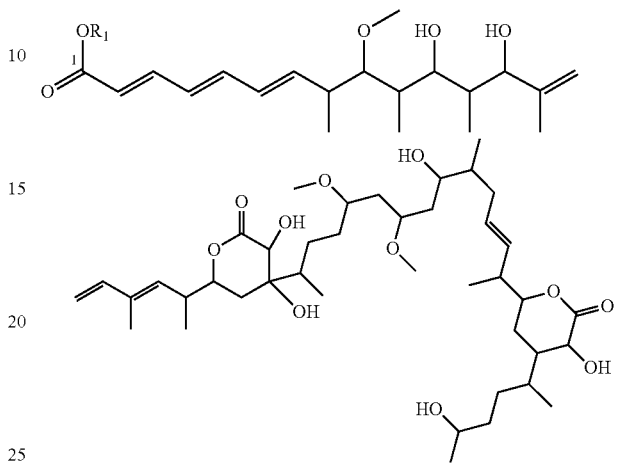

or a phatmaceutically acceptable salt thereof,
where $R_1$ is a hydrogen atom or a ($C_1$-$C_7$) alkyl group.

2. The compound according to claim 1, selected from the following compounds:

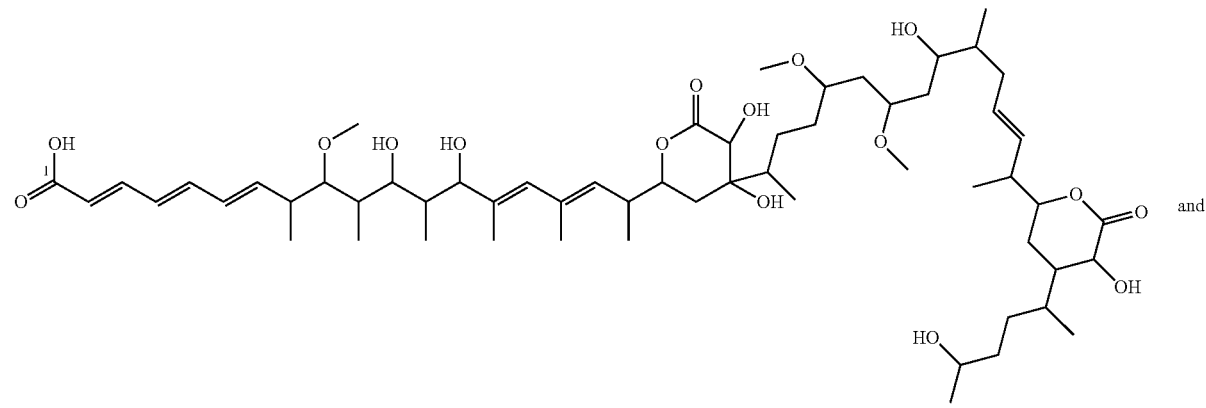

and

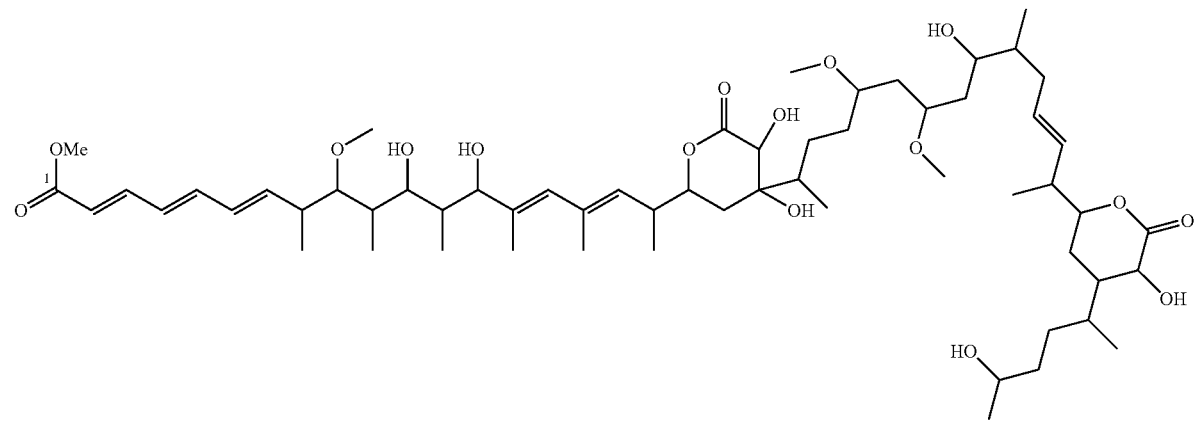

3. A pharmaceutical composition comprising at least one compound according to claim 1 and at least one pharmaceutically acceptable excipient.

4. A method of synthesizing a compound according to claim 1, comprising the following successive steps:
   (i) maceration of lyophilisate of *Hemimycale* sp. sponge with chloroform then with a hydro-ethanolic solution, followed by filtration to give a filtrate, then concentration of said filtrate to give an extract,
   (ii) partition of the extract obtained at the preceding step (i) between water and dichloromethane and separation of the resulting aqueous and organic phases, extraction of the aqueous phase with ethyl acetate and separation of the new resulting aqueous and organic phases, combination of the two organic phases thereby obtained and concentration to give a desalinated extract,
   (iii) taking up the desalinated extract obtained at the preceding step (ii) with a hydro-methanolic solution and hexane, recovery and concentration of the methanolic phase to give a methanolic extract,
   (iv) isolation of the compound of formula (I) with $R_1$=H from the methanolic extract obtained at the preceding step (iii), and
   (v) optionally esterification of the carboxylic acid at C-(1) to give a compound of formula (I) with $R_1$ =($C_1$-$C_7$) alkyl and/or salification of the compound obtained at the preceding step (iv), and isolation of the compound thereby obtained from the reaction mixture.

5. The method of synthesizing according to claim 4, wherein the sponge *Hemimycale* sp. originates from the Torres archipelago, Vanuatu.

6. A method of synthesizing a compound according to claim 1 with $R_1$ representing a ($C_1$-$C_7$) alkyl group from a compound according to claim 1 with $R_1$=H, comprising the following successive steps:
   (a) esterification of the carboxylic acid at C-(1) to give a compound of formula (I) with $R_1$=($C_1$-$C_7$) alkyl,
   (b) optionally salification of the compound obtained at the preceding step (a), and
   (c) isolation of the compound obtained at the preceding step (a) or (b) from the reaction mixture.

* * * * *

UNITED STATES PATENT AND TRADEMARK OFFICE
CERTIFICATE OF CORRECTION

PATENT NO. : 8,569,362 B2  
APPLICATION NO. : 13/504797  
DATED : October 29, 2013  
INVENTOR(S) : Isabelle Carletti et al.

Page 1 of 1

It is certified that error appears in the above-identified patent and that said Letters Patent is hereby corrected as shown below:

ON THE TITLE PAGE:

At item (73), correct the listing of Assignees to read as follows:

--Pierre Fabre Medicament, Boulogne-Billancourt (FR); Centre National de la Recherche Scientifique (CNRS), Paris (FR); Institut de Recherche Pour le Developpement (IRD), Marseille (FR)--.

Signed and Sealed this
Nineteenth Day of August, 2014

Michelle K. Lee
*Deputy Director of the United States Patent and Trademark Office*